United States Patent [19]

Gibson et al.

[11] Patent Number: 5,126,487
[45] Date of Patent: Jun. 30, 1992

[54] PROCESS FOR THE PREPARATION OF 2-ALKYL-4-ACYL-6-TERT-BUTYLPHENOL COMPOUNDS

[75] Inventors: Thomas W. Gibson, Cincinnati; Richard S. Echler, Fairfield, both of Ohio

[73] Assignee: The Procter & Gamble Company, Cincinnati, Ohio

[21] Appl. No.: 675,384

[22] Filed: Mar. 26, 1991

[51] Int. Cl.⁵ .............................................. C07C 45/45
[52] U.S. Cl. ..................................... 568/319; 568/324
[58] Field of Search ............................... 568/319, 324

[56] References Cited

U.S. PATENT DOCUMENTS

| | | | |
|---|---|---|---|
| 4,708,966 | 11/1987 | Loomans et al. | 514/689 |
| 4,847,303 | 7/1989 | Loomans et al. | 514/689 |
| 4,849,428 | 7/1989 | Dobson et al. | 549/307 |
| 4,982,006 | 1/1991 | Hudec | 568/322 |

OTHER PUBLICATIONS

Tedder, J. M., "The Use of Trifluoroacetic Anhydride and Related Compounds in Organic Synthesis", Chemical Reviews, vol. 55 (1955), pp. 787–827.
Galli, C., "Acylation of Arenes and Heteroarenes With In Situ Generated Acyl Trifluoroacetates", Synthesis, Apr. 1979, pp. 303–304.
Nishinaga, A., T. Shimizu, Y. Toyoda & T. Matsuura, "Oxygenation of 2,6-Di-Tert-Butylphenols Bearing an Electron-Withdrawing Group in the 4-Position", Journal of Organic Chemistry, vol. 47 (1982), pp. 2278–2285.

*Primary Examiner*—James H. Reamer
*Attorney, Agent, or Firm*—Milton B. Graff, IV; Jerry J. Yetter; Richard C. Witte

[57] ABSTRACT

The subject invention relates to a process for the preparation of 2-alkyl-4-acyl-6-tert-butylphenol compound having the chemical structure:

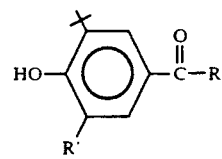

(1)

wherein -R is an aliphatic group having a terminally unsaturated moiety selected from —C≡CH and —CH=C=CH$_2$, and R' is selected from saturated, straight, branched or cyclic alkyl having from 1 to about 10 carbon atoms; the 2-alkyl-4-acyl-6-tert-butylphenol compound being produced in a reaction mixture comprising the corresponding 2-alkyl-6-tert-butylphenol:

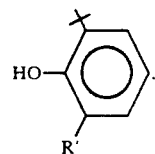

the corresponding carboxylic acid: RCOOH, and trifluoroacetic anhydride.

14 Claims, No Drawings

PROCESS FOR THE PREPARATION OF 2-ALKYL-4-ACYL-6-TERT-BUTYLPHENOL COMPOUNDS

TECHNICAL FIELD

The subject invention relates to a process for preparing certain 2-alkyl-4-acyl-6-tert-butylphenol compounds, where the acyl substituent has a labile moiety, using a modified Friedel-Crafts reaction.

BACKGROUND OF THE INVENTION

Compounds useful as anti-inflammatory agents which are -alkyl-4-acyl-6-tert-butylphenol compounds, especially 4-acyl-2,6-di-tert-butylphenol compounds, and related derivative thereof, where the 4-acyl substituent has a terminally unsaturated moiety, are disclosed in U.S. Pat. No. 4,708,966 issued to Loomans, Matthews & Miller on Nov. 24, 1987; U.S. Pat. No. 4,847,303 issued to Loomans, Matthews & Miller on Jul. 11, 1989; and U.S. Pat. No. 4,949,428 issued to Dobson, Loomans, Matthews & Miller on Jul. 18, 1989. A process for making such compounds is disclosed in U.S. Pat. No. 4,982,006 issued to Hudec on Jan. 1, 1991.

Friedel-Crafts reactions of aromatic hydrocarbons with acyl halides in the presence of a catalyst such as anhydrous aluminum chloride to produce aromatic compounds having an acyl substituent are well-known. But when the acyl moiety has a labile portion, such as the terminal unsaturation of the compounds of interest herein, side reactions often occur resulting in poor yield and purity of the desired product.

The use of trifluoroacetic anhydride to aid the reaction of an aromatic compound and a carboxylic acid is known; see, e.g., Tedder, J.M., "The Use of Trifluoroacetic Anhydride and Related Compounds in Organic Syntheses", Chemical Reviews, Vol. 55 (1955), pp. 787-827; Galli, C., "Acylation of Arenes and Heteroarenes with in situ Generated Acyl Trifluoroacetates", Synthesis, April, 1979, pp. 303-304; Nishinaga, A., T. Shimizu, Y. Toyoda & T. Matsuura, "Oxygenation of 2,6-Di-tert-butylphenols Bearing an Electron-Withdrawing Group in the 4-Position", Journal of Organic Chemistry, Vol. 47 (1982), pp. 2278-2285. However, when the carboxylic acid reactant has a labile portion, such as a terminally unsaturated moiety, unwanted side reactions can occur, see, e.g., Tedder at page 800. Thus, the ability of such a reaction scheme to prepare 2-alkyl-4-acyl-tert-butylphenol compounds where the 4-acyl substituent has a terminally unsaturated moiety was unknown and unpredictable prior to the invention disclosed herein.

It is an object of the subject invention to provide a process for the preparation of certain 2-alkyl-4-acyl-6-tert-butylphenol compounds, where the acyl substituent has a certain terminally-unsaturated moiety.

It is a further object of the present invention to provide a process for the preparation of such compounds from the corresponding 2-alkyl-6-tert-butylphenol and carboxylic acid reactants with good yield.

It is a still further object of the present invention to provide a process for the preparation of such compounds which provides the compounds at high purity and high yield.

SUMMARY OF THE INVENTION

The subject invention relates to a process for the preparation of 2-alkyl-4-acyl-6-tert-butylphenol compound having the chemical structure:

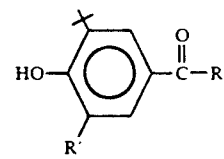

(1)

wherein -R is an aliphatic group having a terminally unsaturated moiety selected from —C≡CH and —CH=C=CH$_2$, and R' is selected from saturated, straight, branched or cyclic alkyl having from 1 to about 10 carbon atoms; the 2-alkyl-4-acyl-6-tert-butylphenol compound being produced in a reaction mixture comprising the corresponding 2-alkyl-6-tert-butylphenol:

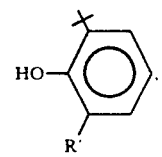

the corresponding carboxylic acid: RCOOH, and trifluoroacetic anhydride.

DETAILED DESCRIPTION OF THE INVENTION

The process of the subject invention comprises a modified Friedel-Crafts reaction among a 2-alkyl-6-tert-butylphenol, a carboxylic acid and trifluoroacetic anhydride according to the following reaction scheme:

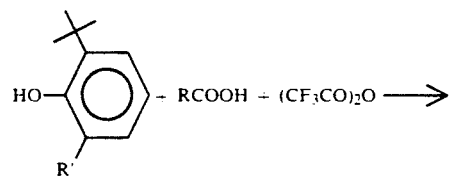

(2)

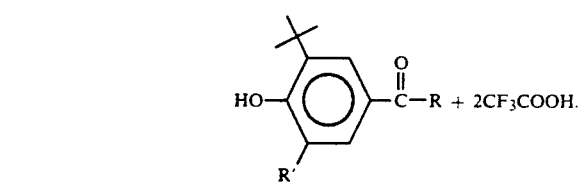

In the above reaction, -R is -B-Y, wherein -Y is selected from —C≡CH and —CH=C=CH$_2$; and —B— is a saturated, unsubstituted, straight or branched alkylene moiety having from 1 to about 12 carbon atoms. -Y is preferably —C≡CH. -B- is preferably straight chain alkylene having from 1 to about 10 carbon atoms, more preferably from about 2 to about 6 carbon atoms, especially 3 carbon atoms.

In the above reaction, R' is saturated, unsubstituted, straight, branched or cyclic alkyl having from about 1 to about 10 carbon atoms. R' is preferably straight or branched alkyl having from 1 to about 8 carbon atoms; most preferably R' is tert-butyl.

In the above reaction, the carboxylic acid reactant has a $pK_a$ of greater than about 3.5, preferably greater than about 4.0.

The above reaction can be carried out in a wide variety of non-polar, liquid solvents which do not react with the above reactants or products, such as hydrocarbons (e.g., hexane, heptane), halogenated hydrocarbons (e.g., dichloroethane), benzene, toluene, acetonitrile, ethers, etc. However, the reactants and reaction products of the subject process are generally miscible as liquids at reasonable temperatures, and no solvent is needed. Therefore, a preferred method for carrying out the above reaction is without the use of a solvent. For large batches, a solvent may be desired to help dissipate the heat of reaction. Heptane and toluene are preferred solvents.

The order of combination of the three reactants is not critical. However, the admixing of trifluoroacetic anhydride with the carboxylic acids of interest is generally highly exo-thermic requiring external cooling. Also, the 2-alkyl-6-tert-butylphenol reactant is often solid at room temperature and must be kept molten during its addition to the trifluoroacetic anhydride/carboxylic acid mixture in order to achieve complete reaction.

A preferred method for carrying out the subject reaction is to dissolve the phenol compound in the carboxylic acid, and to add the trifluoroacetic anhydride slowly. The reaction proceeds spontaneously. When the trifluoroacetic anhydride is added, the resulting reaction is exothermic; external cooling may be used. The trifluoroacetic anhydride is preferably added at a rate such that the temperature of the reaction mixture is controlled as desired.

Another preferred method for carrying out the above reaction is to dissolve the phenol compound in the trifluoroacetic anhydride and to add the carboxylic acid slowly. The reaction proceeds spontaneously. When the carboxylic acid is added, the resulting reaction is exothermic; external cooling may be used. The carboxylic acid is preferably added at a rate such that the temperature of the reaction mixture is controlled as desired.

The temperature of the reaction mixture is preferably controlled at a temperature of from about $-20°$ C. to about $100°$ C., more preferably from about $0°$ C. to about $60°$ C., more preferably still from about $20°$ C. to about $50°$ C.; most preferably from about $40°$ C. to about $45°$ C. After completion of addition of the third reactant, the reaction mixture is preferably stirred and allowed to cool slowly as the reaction is completed, preferably for less than 24 hours, more preferably for from about one-quarter hour to about 4 hours, more preferably still for from about one-half hour to about 2 hours.

The desired reaction will proceed under a wide range of molar ratios of the three reactants. The preferred molar ratio of the three reactants is about 1.0:1.0:1.0. It is preferred that the molar ratio of trifluoroacetic anhydride to carboxylic acid not be substantially greater than 1.0 because the excess trifluoroacetic anhydride will react with the desired reaction product thus reducing its yield. Excess carboxylic acid causes side reactions to occur; a slight excess helps drive the desired reaction to completion. An excess of the phenol reactant is often difficult to separate from the product during subsequent purification. It is preferable that none of the three reactants be incorporated in the reaction mixture in a molar excess of greater than about 30%, based on the total amount of each of the other two reactants incorporated in the reaction mixture; more preferably none is incorporated in the reaction mixture in a molar excess of greater than about 10%.

Under the above conditions, the quantity of desired product achieved from the subject reaction, based on the quantity of limiting reactant, is generally greater than 70%, typically greater than 85%, often greater than 95%. The product yield ultimately obtained is, of course, highly dependent on the purification steps which follow the above reaction step.

In order to obtain high purity product at high yield, the process of the subject invention preferably includes purification steps following the above reaction step comprising a step of crystallization from methanol/water. Preferably the crystallization from methanol/water follows a step of crystallization from hexane.

A highly preferred purification procedure comprises the following steps: (a) dissolving the above completed reaction mixture in hexane at an elevated temperature, preferably removing water-soluble and acidic impurities by extraction with a basic aqueous solution, and preferably contacting the resulting solution with activated charcoal to reduce color and separating out the charcoal; (b) crystallizing product from the hexane solution at a low temperature, separating and drying the product crystals; (c) dissolving the product crystals in methanol at an elevated temperature, and preferably contacting the methanol solution with activated charcoal to remove color and separating out the charcoal; and (d) crystallizing product from the methanol solution by adding water and lowering the temperature, separating and drying the product crystals.

In step (a) above, the completed reaction mixture is dissolved in hexane, preferably at a temperature of from about $50°$ C. to about $69°$ C., more preferably from about $65°$ C. to about $69°$ C. The weight ratio of hexane:reaction mixture is preferably from about 20:1 to about 5:1, more preferably from about 10:1 to about 5:1. If the resulting solution is not colorless, color can be removed by the addition of activated charcoal and mixing followed by filtration to remove the charcoal.

Before crystallizing product from the hexane solution in step (b) above, the hexane solution is preferably concentrated by evaporating off a portion of the hexane. Preferably the resulting concentrate has a ratio of hexane to reaction product of from about 10:1 to about 3:1, more preferably from about 8:1 to about 4:1. The preferred temperature for crystallizing product from the hexane solution is from about $25°$ C. to about $0°$ C., more preferably from about $10°$ C. to about $0°$ C. The crystals are removed from the supernatant liquid, preferably by filtration, dried, preferably under vacuum and at a temperature of less than about $30°$ C.

In step (c) of the above process, the crystals from step (b) are dissolved in methanol, preferably at a temperature of from about $45°$ C. to about $65°$ C., more preferably from about $60°$ C. to about $65°$ C. The weight ratio of methanol to solids is from about 20:1 to about 3:1, preferably from about 10:1 to about 4:1. If the resulting solution is not colorless, color can be removed by the addition of activated charcoal and mixing followed by filtration to remove the charcoal.

In step (d), water is added to the methanol solution of step (c) and the resulting mixture is cooled, preferably to a temperature of from about $20°$ C. to about $0°$ C., more preferably from about $10°$ C. to about $0°$ C. The weight ratio of methanol:water is preferably from about 20:1 to about 3:1, preferably from about 10:1 to about 4:1. The product crystals are removed from the supernatant liquid, preferably by filtration. The crystals are dried, preferably in a vacuum oven at a temperature of less than about 45° C.

The following examples further describe and demonstrate the preferred embodiments within the scope of the subject invention. The examples are given solely for the purpose of illustration, and are not to be construed as limitations of the subject invention, since many variations thereof are possible without departing from its spirit and scope.

EXAMPLES 1–20

Table 1 below is a summary of the production of laboratory-scale (about 30 g product per batch) batches of 4-5'-hexynoyl)-2,6-di-tert-butylphenol produced by reacting 2,6-di-tert-butyl-phenol, 5-hexynoic acid and trifluoroacetic anhydride under various reaction conditions.

In Table 1, the Method number refers to the following procedures:

Method 1: The 5-hexynoic acid and trifluoroacetic anhydride are mixed together with ice cooling. The 2,6-ditert-butylphenol is then added all at once and the reaction mixture is stirred for the time indicated.

Method 2: The 2,6-di-tert-butylphenol and trifluoroacetic anhydride are mixed together at room temperature, and the 5-hexynoic acid is added rapidly. The reaction mixture is stirred for the time indicated.

Method 3: The 2,6-di-tert-butylphenol and 5-hexynoic acid are mixed at room temperature, and the trifluoroacetic anhydride is added at a controlled rate. After addition of the trifluoroacetic anhydride is completed, the reaction mixture is stirred for the indicated time.

Method 4: The 2,6-di-tert-butylphenol and 5-hexynoic acid are dissolved in a solvent. The superscript letter in parenthesis after the 4 indicates the solvent used: (a) hexane, (b) toluene, (c) acetonitrile with phosphoric acid, (d) acetonitrile. The trifluoroacetic anhydride is added at a controlled rate.

The Ratio indicated for each Example in Table 1 is the molar ratio of total amounts of 5-hexynoic acid:2,6-di-tert-butyl-phenol:trifluoroacetic anhydride added to the mixture.

The Temp. indicated for each Example in Table 1 is the maximum temperature reached by the reaction mixture during the reaction. For the Examples where the third reactant is added all at once or rapidly, the reaction temperature comes to the indicated peak temperature and then slowly cools throughout the reaction time. For the Examples of Methods 3 and 4 where the trifluoroacetic anhydride is added at a controlled rate, a temperature close to that indicated is maintained throughout the addition, and then the reaction mixture is allowed to cool slowly. Example 19 differs in that the 50° C. temperature is maintained throughout the 5-hour time of stirring by heating.

After completion of the reaction, the contents of the reaction mixture are analyzed to determine (1) the amount of 2,6-di-tert-butylphenol remaining, (2) the amount of 4-(5'-hexynoyl)-2,6-di-tert-butylphenol produced, and (3) other products of the reaction. The percent Conversion shown in Table 1 is 100 minus the percent of unreacted 2,6-di-tert-butyl-phenol (based on the starting amount of this reactant). The percent Selectivity shown in Table 1 is the percent of desired product to total products in the completed reaction mixture.

TABLE 1

| Example | Method | Ratio | Temp. (°C.) | Time (hrs) | Conversion (%) | Selectivity (%) |
|---|---|---|---|---|---|---|
| 1 | 1 | 1.3:1.0:1.5 | 23 | 3 | 100 | 93 |
| 2 | 1 | 1.0:1.0:1.1 | 0 | 2.5 | 77 | 98 |
| 3 | 1 | 1.0:1.0:1.1 | 55 | 2.5 | 99 | 81 |
| 4 | 1 | 1.1:1.0:1.3 | 23 | 1.3 | 98 | 92 |
| 5 | 1 | 1.1:1.0:1.3 | 23 | 1.3 | 99 | 94 |
| 6 | 2 | 1.1:1.0:1.3 | 65 | 0.75 | 99 | 84 |
| 7 | 2 | 1.2:1.0:1.3 | 63 | 0.33 | 99 | 89 |
| 8 | 3 | 1.1:1.0:1.3 | 75 | 0.25 | 99 | 84 |
| 9 | 3 | 1.1:1.0:1.1 | 36 | 3 | 99 | 96 |
| 10 | 3 | 1.1:1.0:1.0 | 78 | 0.25 | 98 | 99 |
| 11 | 3 | 1.0:1.1:1.0 | 83 | 3 | 93 | 96 |
| 12 | 3 | 1.0:1.1:1.0 | 102 | 1.5 | 96 | 80 |
| 13 | 3 | 1.0:1.0:1.0 | 80 | 0.33 | 98 | 86 |
| 14 | 3 | 1.0:1.0:1.0 | 68 | 1 | 99 | 87 |
| 15 | 4(a) | 1.0:1.0:1.0 | 62 | 0.5 | 97 | 91 |
| 16 | 4(a) | 1.0:1.0:1.0 | 50 | 1 | 98 | 87 |
| 17 | 4(b) | 1.0:1.0:1.0 | 23 | 22 | 84 | 81 |
| 18 | 4(c) | 1.0:3.0:3.7 | 31 | 2 | 100 | 90 |
| 19 | 4(d) | 1.1:1.0:1.0 | 50 | 5 | 86 | 92 |
| 20 | 3 | 1.0:1.0:0.5 | 35 | 22 | 80 | 98 |

EXAMPLE 21

Method 3 above is used to produce 4-(4'-pentynoyl)-2,6-di-tert-butylphenol by reacting 2,6-di-tert-butyl-phenol and 4-pen-tynoic acid and trifluoroacetic anhydride at a molar ratio of 1.0:1.0:1.0 at a maximum temperature of 36° C. with a reaction time of 2 hours after addition of the trifluoroacetic anhydride.

EXAMPLE 22

Method 3 above is used to produce 4-(4',5'-hexadienoyl)-2,6-di-tert-butylphenol by reacting 2,6-4,5-hexadienoic acid and trifluoroacetic anhydride at a molar ratio of 1.0:1.0:1.0 at a maximum temperature of 56° C. with stirring for 2 hours after addition of the trifluoroacetic anhydride.

EXAMPLE 23

Method 3 above is used to produce 4-(10,-undecynoyl)-2,6-di-tert-butylphenol by reacting 2,6-di-tert-butylphenol with 10-undecynoic acid and trifluoroacetic anhydride at a molar ratio of 1.0:1.0:1.0 at a maximum temperature of 45° C. with stirring for 2 hours after addition of the trifluoroacetic anhydride.

EXAMPLE 24

The following is an exemplary synthesis and purification of 4-(5'-hexynoyl)-2,6-di-tert-butylphenol using a process of the subject invention.

2,6-Di-tert-butylphenol (5496 g, Ethyl Corp.) is melted on a warm water bath and charged into a 50L three-neck, round-bottom flask equipped with an air driven stirrer, stir shaft, large Teflon stirring paddle, addition funnel, thermometer, and reflux condenser. The apparatus is assembled in a stainless steel cooling bath. To the gently stirred liquid is added 5-hexynoic acid (3288 g, Farchan Laboratories). Trifluoroacetic anhydride (5872 g, Halocarbon Inc.) is added through the addition funnel at such a rate to keep the reaction temperature at 40°–45° C. throughout the time of addition. After the addition, which requires about 1 hour, the resulting solution is stirred an additional hour at 30°-40° C. The reaction mixture is diluted with 52L of hexane, extracted twice with 20L of 5% potassium carbonate, once with 20L of water, and then treated with 400 g of Darco G-60 activated carbon at reflux for 15 minutes. The hot mixture is filtered through Celite, washed with 800 mL of hexane, and concentrated to a final volume of 36 L on a rotary evaporator. Crystallization with slow agitation at 0°-3° C. followed by filtration and drying in a vacuum oven at 40°-45° C. gives 5960 g of crude product. The crude product (5935 g) is dissolved in 29.6 L of methanol and treated at reflux for 15 minutes with 550 g of activated carbon. The hot mixture is filtered through Celite. Water (5830 mL) is added. Crystallization is accomplished with slow agitation in an ice bath. Filtration gives 5140 g of purified product, after drying in a vacuum oven at 40°-45° C. and 27-28 in Hg.

While particular embodiments of the subject invention have been described, it will be obvious to those skilled in the art that various changes and modifications to the processes disclosed herein can be made without departing from the spirit and scope of the invention. It is intended to cover, in the appended claims, all such modifications that are within the scope of this invention.

What is claimed is:

1. A process for the preparation of a 2-alkyl-4-acyl-6-tert-butylphenol compound having the structure:

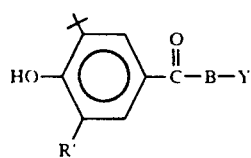

wherein -Y is —C≡CH or —CH=CH=CH$_2$; -B- is saturated, unsubstituted, straight or branched alkylene having from 1 to about 12 carbon atoms; and -R, is saturated, unsubstituted, straight, branched or cyclic alkyl having from 1 to about 10 carbon atoms; the 2-alkyl-4-acyl-6-tert-butylphenol compound being produced in a reaction mixture comprising a 2-alkyl-6-tert-butylphenol reactant having the structure:

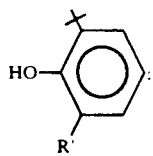

a carboxylic acid reactant having the structure Y-B-COOH; and trifluoroacetic anhydride reactant.

2. The process of claim 1 wherein -B- is straight-chain alkylene, and -R' is straight-chain alkyl having from 1 to 3 carbon atoms or branched alkyl having from 3 to about 8 carbon atoms.

3. The process of claim 2 wherein -R' is tert-butyl.

4. The process of claim 3 wherein -Y is —C≡CH.

5. The process of claim 4 wherein -B- is —CH$_2$CH$_2$CH$_2$—.

6. The process of claim 1 wherein the reaction mixture consists essentially of the three reactants and reaction products thereof.

7. The process of claim 4 wherein the reaction mixture consists essentially of the three reactants and reaction products thereof.

8. The process of claim 5 wherein the reaction mixture consists essentially of the three reactants and reaction products thereof.

9. The process of any of claims 1, 3 and 8 wherein any molar excess of any reactant is no more than about 30%.

10. The process of any of claims 1, 3, 5, 6 and 8 wherein any molar excess of any reactant is no more than about 10%.

11. A process for the preparation of a purified crystalline product, the product being greater than about 98% of a 2-alkyl-4-acyl-6-tert-butylphenol compound having the structure:

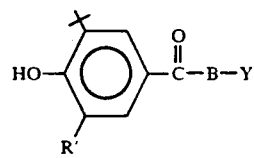

wherein -Y is —C≡CH or —CH=CH=CH$_2$; -B- is saturated, unsubstituted, straight or branched alkylne having from 1 to about 12 carbon atoms; and -R' is saturated, unsubstituted, straight, branched or cyclic alkyl having from 1 to about 10 carbon atoms; comprising the following steps:

(a) producing the 2-alkyl-4-acyl-6tert-butylphenol compound in a reaction mixture comprising a 2-alkyl-6-tert-butylphenol reactant having the structure:

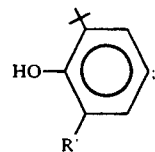

a carboxylic acid reactant having the structure Y-B-COOH; and trifluoroacetic anhydride reactant; and (b) crystallizing the compound from methanol/water, separating resulting crystals from supernatant liquid and drying the crystals.

12. The process of claim 11 wherein between steps (a) and (b) there is a step of crystallizing the compound from hexane, separating resulting crystals from supernatant liquid and drying the crystals.

13. A process for the preparation of a purified crystalline product, the product being greater than about 98% of a 2-alkyl-4-acyl-6-tert-butylphenol compound having the structure

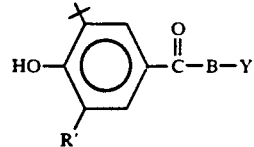

wherein -Y is —C≡CH or —CH=CH=CH$_2$; -B- is saturated, unsubstituted, straight or branched alkylene having from 1 to about 12 carbon atoms; and -R' is saturated, unsubstituted, straight, branched or cyclic alkyl having from 1 to about 10 carbon atoms; comprising the following steps:

(a) producing the 2-alkyl-4-acyl-6-tert-butylphenol compound in a reaction mixture comprising a 2-alkyl-6-tert-butylphenol reactant having the structure:

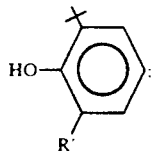

a carboxylic acid reactant having the structure Y-B-COOH; and trifluoroacetic anhydride reactant;

(b) dissolving the reaction mixture in hexane at an elevated temperature;

(c) contacting the solution of step (b) with activated charcoal and removing the charcoal;

(d) crystallizing the compound from the solution of step (c) at low temperature; separating and drying resulting crystals;

(e) dissolving the crystals from step (d) in methanol at an elevated temperature;

(f) contacting the solution of step (e) with activated charcoal and removing the charcoal;

(g) crystallizing the compound from the solution of step (f) by adding water and lowering the temperature, separating and drying resulting crysals.

14. The process of claim 12 wherein -$R^1$ is tert-butyl, -Y is —C≡CH, and -B- is —$CH_2CH_2CH_2$—.

* * * * *

UNITED STATES PATENT AND TRADEMARK OFFICE
CERTIFICATE OF CORRECTION

PATENT NO. : 5,126,487

DATED : June 30, 1992

INVENTOR(S) : Thomas W. Gibson and Richard S. Echler

It is certified that error appears in the above-identified patent and that said Letters Patent is hereby corrected as shown below:

Column 1, line 15, "-alkyl-4-acyl-6-tert-butylphenol" should be
--2-alkyl-4-acyl-6-tert-butylphenol--.

Column 2, line 30, "R" should be --R'--.

Column 5, line 26, "2,6-ditert-butylphenol" should be
--2,6-di-tert-butylphenol--.

Column 6, lines 36-37, "2,6-4,5-hexadienoic acid" should be
--2,6-di-tert-butylphenol with 4,5-hexadienoic acid--.

Column 7, line 38, "-R." should be -- -R'--.

UNITED STATES PATENT AND TRADEMARK OFFICE
CERTIFICATE OF CORRECTION

PATENT NO. : 5,126,487

DATED : June 30, 1992

INVENTOR(S) : Thomas W. Gibson and Richard S. Echler

It is certified that error appears in the above-indentified patent and that said Letters Patent is hereby corrected as shown below:

Column 8, line 28, "2-alkyl-4-acyl-6tert-butylphenol" should be
--2-alkyl-4-acyl-6-tert-butylphenol--.

Signed and Sealed this

Twenty-eighth Day of December, 1993

Attest:

BRUCE LEHMAN

*Attesting Officer*  *Commissioner of Patents and Trademarks*